(12) United States Patent
Takagi (10) Patent No.: US 7,208,284 B2
(45) Date of Patent: Apr. 24, 2007

(54) METHOD FOR MEASURING POLYAMINES IN ERYTHROCYTES, DIAGNOSTIC METHOD AND KIT FOR MEASURING POLYAMINES IN ERYTHROCYTES

(75) Inventor: Kenji Takagi, Mizunami (JP)

(73) Assignee: National University Corporation Nagoya University, Nagoya-shi (JP)

( * ) Notice: Subject to any disclaimer, the term of this patent is extended or adjusted under 35 U.S.C. 154(b) by 0 days.

(21) Appl. No.: 11/003,416

(22) Filed: Dec. 6, 2004

(65) Prior Publication Data

US 2005/0277166 A1   Dec. 15, 2005

(30) Foreign Application Priority Data

Jun. 9, 2004   (JP) .............................. 2004-170845

(51) Int. Cl.
*G01N 33/00* (2006.01)

(52) U.S. Cl. .................................... 435/7.25

(58) Field of Classification Search ............... 435/7.25
See application file for complete search history.

(56) References Cited

U.S. PATENT DOCUMENTS

| | | | | |
|---|---|---|---|---|
| 4,617,263 A | * | 10/1986 | Yamada et al. | 435/25 |
| 4,988,724 A | * | 1/1991 | Ajani et al. | 514/399 |
| 2002/0025546 A1 | * | 2/2002 | Komori et al. | 435/28 |

OTHER PUBLICATIONS

Kaur-Sawhney, Ravindar et al; "Polyamine Oxidase in Oat Leaves: A Cell Wall-Localized Enzyme"; 1981; Plant Physiology; vol. 68, pp. 494-498.*

Cervelli, Manuela et al; "A barley pl;oyamine oxidase isoform iwht distinct structural features and subcellular localization"; Jul. 2001; European Journal of Biochemistry; vol. 268, pp. 3816-3830.*

William G. Dykstra, Jr, et al., "Spermidine in Regenerating Liver: Relation to Rapid Synthesis of Ribonucleic Acid", Science, New Series, vol. 149, No. 3682, Jul. 23, 1965, pp. 428-429.

Diane Russell, et al., "Amine Synthesis in Rapidly Growing Tissues: Ornithine Decarboxylase Activity in Regenerating Rat Liver, Chick Embryo, and Various Tumors", Proc. Natl. Acad. Sci. U.S.A., vol. 60, May 8, 1968, pp. 1420-1427.

Kimiyasu Isobe, et al., "A Rapid Enzymatic Assay for Total Blood Polyamines" Clinical Biochemistry, vol. 20, Jun. 1987, pp. 157-161.

Masato Okada, et al., "Polyamine Sanka Koso" Tanpakushitsu Kakusan Koso, vol. 26, No. 9, 1981, pp. 1471-1479.

T. A. Smith, "Purification and Properties of the Polyamine Oxidase of Barley Plants", Phytochemistry, vol. 11, 1972, pp. 899-910.

Kenji Takagi, et al., "A Sensitive Colorimetric Assay for Polyamines in Erythrocytes using Oat Seeding Polyamine Oxidase", Clinica Chimica Acta, vol. 340, 2004, p. 219 (Abstract only).

* cited by examiner

*Primary Examiner*—Christopher R. Tate
*Assistant Examiner*—Amanda P. Wood
(74) *Attorney, Agent, or Firm*—Oblon, Spivak, McClelland, Maier & Neustadt, P.C.

(57) ABSTRACT

A method for measuring polyamines in erythrocytes in which a polyamine oxidase having a substrate specificity to spermine and spermidine or a polyamine oxidase having a substrate specificity to spermine only is used, an eluate in erythrocytes separated and purified from blood is reacted with these enzymes, and hydrogen peroxide formed is determined with a highly sensitive chromogen1 such as a diphenylamine-based chromogen. A method for measuring amounts of polyamines in erythrocytes easily with high precision. The method is effective for diagnosis of certain disease conditions or physiological conditions or the like.

12 Claims, 1 Drawing Sheet

FIG. 1

METHOD FOR MEASURING POLYAMINES IN ERYTHROCYTES, DIAGNOSTIC METHOD AND KIT FOR MEASURING POLYAMINES IN ERYTHROCYTES

BACKGROUND OF THE INVENTION

1. Field of the Invention

The present invention relates to a method for measuring polyamines in erythrocytes, a diagnostic method and a kit for measuring polyamines in erythrocytes. More specifically, the invention relates to a method for measuring polyamines in erythrocytes in which amount(s) of spermine (hereinafter referred to also as "Spm") and/or spermidine (hereinafter referred to also as "Spd") in erythrocytes can selectively be measured for studies or clinical purposes, a diagnostic method in which disease conditions or physiological conditions of specimens can be diagnosed using the results of the measuring method, and a kit for measuring polyamines in erythrocytes which can be used in such a measuring method or diagnostic method.

2. Description of the Related Art

[Study of In-Vivo Polyamines]

Polyamines inherently include basic hydrocarbon compounds having two or more primary amino groups or secondary amino groups. However, as polyamines found in vivo, putrescine, cadaverine, spermine, spermidine and the like have been known. Of these, spermine is N,N'-bis(3-aminopropyl)-1,4-diaminobutane [$NH_2(CH_2)_3NH(CH_2)_4NH(CH_2)_3NH_2$]. Spermidine is N-(3-aminopropyl)-1,4-diaminobutane [$NH_2(CH_2)_3NH(CH_2)_4NH_2$]. When merely "polyamines" are referred to, they indicate these polyamines found in vivo.

Polyamines are present in large quantities in cells of all organisms ranging from viruses to humans. It has been known that although polyamines are compounds having very simple structures, they interact with various acidic high-molecular materials to exhibit various physiological activities. In recent years, polyamines have attracted much interest in relation to proliferation and differentiation of cells in particular. For example, their relations to DNA synthesis, RNA synthesis, protein synthesis and the like have been studied in the wide range using a regenerated liver and the like. A knowledge which can be applied at clinical levels has been increased.

For example, Dykstra et al. have reported in the following "Literature 1" that after partial excision of the rat liver, the concentration of spermidine is increased for 24 hours, while the concentration of spermine is not increased. In this case, an accumulation rate of the polyamine is nearly the same as an increase rate of RNA synthesis in the regenerated liver, and incorporation of putrescine intravenously injected and synthesis of spermidine are increased within 2 hours after operation of the liver excision. The polyamines are measured using an extract of the rat liver.

Literature 1: William G. Dykstra, Jr.; Edward J. Herbst "Spermidine in Regenerating Liver: Relation to Rapid Synthesis of Ribonucleic Acid" Science, New Series, Vol. 149, No. 3682 (Jul. 23, 1965), 428–429

Russell et al. have reported in the following "Literature 2" that abnormally high polyamine values in urine were identified in patients with various cancers. After this report, a large number of reports have been made on analysis of polyamines in urine, serum, erythrocytes and the like as an index of effects in a diagnostic method, a chemotherapy and the like of malignant tumors.

Literature 2: Diane Russell, Solomon H. Snyder "Amine Synthesis in Rapidly Growing Tissues: Ornithine Decarboxylase Activity in Regenerating Rat Liver, Chick Embryo, and various Tumors" Proc. Natl. Acad. Sci. U.S.A., 1968; 60:1420–1427

[Method for Measuring Polyamines]

Under these circumstances, various methods for measuring polyamines in biological samples have been proposed, and some of them have already been put to practical use or are being put to practical use. One of the typical methods is an HPLC method (high-performance liquid chromatography method), which has been utilized for measuring polyamines in blood or polyamines in urine. However, this method is, as well known, considered to be intricate in processing and hardly spread routinely as a common clinical examination method.

Meanwhile, Kubota et al. exploited a method for measuring polyamines in urine using enzymes. This measuring method has been reported in "Igaku no Ayumi" 124(1), 22–24, 1983 and the like. Since this method was exploited, the measurement of total polyamines in urine has been routinized as auxiliary diagnosis of all malignant tumors or as an auxiliary method for estimating therapeutic effects in surgical treatment, administration of antitumor agents, radiotherapy and the like on malignant tumors. Kits for measuring polyamines in urine have been also on the market.

Furthermore, Isobe et al. have reported in the following "Literature 3" the measurement of total polyamines in blood by an enzymatic method.

Literature 3: Kimiyasu Isobe, Hideaki Yamada, Yasuko Soejima, Shogo Otsuji, "A Rapid Enzymatic Assay for Total Blood Polyamines" Clin Biochem, Vol. 20, pp. 157–161, 1987

[Enzymes Used in an Enzymatic Method]

Polyamine oxidases are used in the Kubota et al method or the Isobe et al method. Okada et al have reported properties and the like of various polyamine oxidases in the following "Literature 4". According to this report, polyamine oxidases are roughly classified into those having a wide-range substrate specificity including a specificity to monoamines and those which specifically react with polyamines including diamines. As an example of enzymes which specifically react with polyamines, an oat-derived polyamine oxidase having a substrate specificity to spermine and spermidine only has been introduced.

Literature 4: Masato Okada, Seiichi Kawashima, Kazutomo Imabori, "Polyamine Sanka Koso" Tanpakushitsu Kakusan Koso vol. 26, No. 9 (1981)

According to the following "Literature 5" of Smith, it has been reported that a barley-derived polyamine oxidase allows specific enzymolysis of spermine with fixed pH.

Literature 5: T. A. Smith "Purification and Properties of the Polyamine Oxidase of Barley Plants" Phytochemistry, 1972, Vol. 11, pp. 899 to 910

Incidentally, a method for measuring polyamines by the foregoing Kubota et al enzymatic method is not said to be simple enough because polyamines in urine are in a conjugated form and therefore require pretreatment of hydrolysis thereof into a free form. Further, when urine is used, a secretory amount of urine water varies with a difference in water intake or action state, a difference in season and the like, so that the method is liable to change in concentrations due to these causes. Urine serves to properly secrete excess water or a waste material for keeping homeostasis (acid-base equilibrium and the like) of body fluids, and concentrations in urine do not altogether indicate directly concentrations within the body. Thus, the method is not satisfactory either as a diagnostic method in view of sensitivity.

In the method for measuring polyamines by the Isobe et al enzymatic method, there is still room for improvement in simplicity because two types of amine oxidases derived from bacteria and fungi are used and a two-step enzymatic reaction is needed.

These methods for measuring polyamines are to measure total polyamines in urine or blood, and do not specifically measure specific polyamine compounds. Accordingly, disease conditions or physiological conditions which can be diagnosed are naturally restricted, and the methods are considered to be problematic in diagnostic precision regarding some types of disease conditions or physiological conditions.

SUMMARY OF THE INVENTION

The invention aims to provide a method for measuring polyamines which is constructed simply and high enough in sensitivity as a diagnostic method and which can specifically measure specific polyamine compounds that have attracted much interest in relation to various disease conditions or physiological conditions. The invention further aims to enable advantageous and effective diagnosis of certain disease conditions or physiological conditions by this method for measuring polyamines.

The first aspect of the invention is a method for measuring polyamines in erythrocytes, comprising a step of reacting an eluate of erythrocytes separated and purified from blood with a polyamine oxidase having a substrate specificity to spermine and spermidine, and a step of determining hydrogen peroxide formed in the foregoing step with a highly sensitive chromogen to measure a total amount of spermine and spermidine in erythrocytes.

The type of above stated "highly sensitive chromogen" is not necessarily limited. However, diphenylamine-based highly sensitive chromogen is one of the most preferable chromogen.

The present inventor has focused on Spm and Spd of in-vivo polyamines. As described in the foregoing Literature 1 and Literature 2 or many other study reports, Spm and Spd have quite a high value as an index substance in comparison to the other in-vivo polyamines. The measurement of the total amount of Spm and Spd gives quite an effective diagnostic index on various disease conditions or physiological conditions of patients. More specifically, the total amount of Spm and Spd in erythrocytes is effective as a diagnostic index of cancers, and also effective for estimating therapeutic effects in performing surgical treatment, administration of antitumor agents, radiotherapy and the like on malignant tumors. A large number of reports will be made almost certainly in near future regarding specific disease conditions or physiological conditions in which the total amount of Spm and Spd in erythrocytes is an effective diagnostic index.

Since polyamine oxidases having a substrate specificity to Spm and Spd exist, the present inventor has successfully constructed a method for measuring polyamines in which the total amount of Spm and Spd can specifically be measured by the measuring method using such enzymes. Consequently, a new method for measuring polyamines has been provided which has wide-ranging applications and enables exact diagnosis.

The present inventor has focused especially on Spm and Spd in erythrocytes. Polyamines are present in erythrocytes at higher concentrations than in urine or plasma, and are mainly Spm and Spd in a free form. Accordingly, measurement with high sensitivity is possible, and further the pretreatment for obtaining polyamines in a free form as required in the foregoing Kubota et al enzymatic method is unnecessary.

Further, a measuring method for blood or specific ingredients thereof involves, as pointed out generally, blood sampling which gives some burden to patients. For this reason, it has been required to reduce an amount of blood sampled as much as possible. In this sense, a measurement system has been also required to be designed especially with high sensitivity. The first aspect of the invention has achieved these objects by the designing of the measurement system that an amount of hydrogen peroxide formed by an enzymatic reaction is measured by coloration with a highly sensitive chromogen, more preferably, with a diphenylamine-based chromogen.

According to the measuring method in the first aspect, on the basis of the foregoing various characteristic points, the total amount of Spm and Spd can effectively be measured using packed erythrocytes in a small amount of 0.5 mL or less for one measurement, as will be later described in Examples. This point has a significant meaning from a clinical consideration of reducing burden of patients.

The measuring method of the first aspect can be used for various clinical diagnoses such as diagnosis for prognosis of organ excision or organ transplantation and diagnosis of cancers and further provide a potent method for basic studies, for example, studies on differentiation and proliferation of cells and studies on DNA synthesis, RNA synthesis or protein synthesis.

The second aspect of the invention is the method for measuring polyamines in erythrocytes according to the first aspect, wherein the polyamine oxidase is an enzyme derived from a plant selected from a gramineous plant group including at least oats.

The type and the origin of the polyamine oxidase used in the first aspect are not limited so long as it has a substrate specificity to spermine and spermidine. However, a polyamine oxidase derived from a gramineous plant, especially an oat seedling-derived polyamine oxidase (hereinafter referred to also as "OSPO") can preferably be mentioned.

The third aspect of the invention is the method for measuring polyamines in erythrocytes according to the first aspect or the second aspect, wherein the highly sensitive chromogen is a metal salt of N-(carboxymethylaminocarbonyl)-4,4'-bis(dimethylamino)-diphenylamine.

The type of the highly sensitive chromogen used in the first aspect or the second aspect is not necessarily limited. However, a chromogen having such a high sensitivity that spermine and spermidine in packed erythrocytes in amounts of 0.5 mL or less as samples can effectively be detected through formation of hydrogen peroxide. For example, a metal salt of N-(carboxymethylaminocarbonyl)-4,4'-bis(dimethylamino)-diphenylamine can preferably be mentioned. As the metal salt, preferably, an alkali metal salt, more preferably a sodium salt can be mentioned. N-(carboxymethylaminocarbonyl)-4,4'-bis(dimethylamino)diphenylamine sodium salt is hereinafter referred to also as "DA-64".

The fourth aspect of the invention is a method for measuring polyamines in erythrocytes, comprising a step of reacting an eluate of erythrocytes separated and purified from blood with a polyamine oxidase having a substrate specificity to spermine, and a step of determining hydrogen peroxide formed in the foregoing step with a highly sensitive chromogen to measure an amount of spermine in erythrocytes.

The type of above stated "highly sensitive chromogen" is not necessarily limited. However, diphenylamine-based highly sensitive chromogen is one of the most preferable chromogen.

Focusing on spermine only of in-vivo polyamines has a significant meaning too. The present inventor has not yet understood well to what disease conditions or physiological conditions of patients the Spm amount in erythrocytes gives an effective diagnostic index. However, from various physiological activities of Spm which have been reported at levels of basic studies, a large number of reports will be made almost certainly in near future on disease conditions or physiological conditions for which the Spm amount is an effective diagnostic index.

The measurement of the Spm amount in erythrocytes is useful for at least the following points. That is, according to the foregoing Literature 1, the amount of spermidine is effective as a diagnostic index for prognosis of excision or transplantation of organs such as the liver. When the measured value (Spm+Spd) according to the method of the first aspect and the measured value (Spm) according to the method of the fourth aspect are obtained on the same sample collected from the same specimen, the Spd amount in this sample can easily be calculated.

From these points, a new method for measuring polyamines which has wide-ranging applications and enables the exact diagnosis is provided in the fourth aspect also as in the first aspect. Since Spm in erythrocytes is employed, the highly sensitive measurement is possible. Further, pretreatment for obtaining free polyamines is unnecessary. In addition, there is a merit that the measurement can be conducted on the basis of packed erythrocytes in a small amount of 0.5 mL or less for one measurement. Moreover, the fourth aspect, like the first aspect, can provide a potent study method to basic studies besides various clinical diagnostic purposes.

The measurement of the Spm amount has also a significant meaning in the agricultural field, which has no direct bearing on the invention, though. For example, it has been recognized that a tobacco leaf infected with tobacco mosaic virus accumulates Spm in an amount which is more than 20 times that of a normal tobacco leaf and the infection is not spread over the whole plant from such a leaf. With respect to a general function of Spm, it is said that Spm ralates to phosphorylation of proteins participating in signal transmission. At any rate, it is said that in tobacco leaves, Spm induces pathogen resistance in the virus infection through induction of a specific protein group. Accordingly, the measurement of the Spm amount is expected to give a significant knowledge in production of plants with resistance to viral pathogens and the like.

The fifth aspect of the invention is the method for measuring polyamines in erythrocytes according to the fourth aspect, wherein the polyamine oxidase is an enzyme derived from a plant selected from a gramineous plant group including at least barley.

The type or origin of the polyamine oxidase used in the fourth aspect is not limited so long as it has a substrate specificity to spermine. However, a polyamine oxidase derived from the gramineous plant, especially a barley seedling-derived polyamine oxidase (hereinafter referred to also as "BSPO") can preferably be mentioned.

The sixth aspect of the invention is the method for measuring polyamines in erythrocytes according to the fourth aspect or the fifth aspect, wherein the highly sensitive chromogen is a metal salt of N-(carboxymethylaminocarbonyl)-4,4'-bis(dimethylamino)-diphenylamine.

The type of the highly sensitive chromogen used in the fourth aspect or the fifth aspect is not necessarily limited. However, a diphenylamine-based chromogen having such a high sensitivity that spermine in packed erythrocytes in an amount of 0.5 mL or less as a sample can effectively be detected through formation of hydrogen peroxide is preferable. For example, DA-64 and metal salts similar thereto can be mentioned.

The seventh aspect of the invention is a method for measuring polyamines in erythrocytes, comprising a step of obtaining a calculated value C of a spermidine amount in erythrocytes by subtracting the following measured value B from the following measured value A on the basis of the same sample of the same specimen.

Measured value A: measured value of a total amount of spermine and spermidine in erythrocytes which is obtained by the method for measuring polyamines in erythrocytes according to any of the first to third aspects.

Measured value B: measured value of spermine in erythrocytes which is obtained by the method for measuring polyamines in erythrocytes according to any of the fourth to sixth aspects.

In the seventh aspect, the calculated value C of the Spd amount in erythrocytes can easily be obtained by subtracting the measured value B of the Spm amount in erythrocytes from the measured value A of the total amount of Spm and Spd in erythrocytes on the same sample of the same specimen.

This calculated value C is effective as a diagnostic index for prognosis of excision or transplantation of organs such as the liver. In addition, a large number of reports will be made almost certainly in near future on disease conditions or physiological conditions for which the Spm amount in erythrocytes is an effective diagnostic index.

The eighth aspect of the invention is a diagnostic method comprising a step of conducting diagnosis of a specimen using as an index at least one of the measured value A, the measured value B and the calculated value C according to the seventh aspect on disease conditions or physiological conditions identified to be related with these indexes.

As in the eighth aspect, the diagnosis of the specimen can be conducted on the disease conditions or the physiological conditions easily with good precision using as an index at least one of the measured value A which is the total amount of Spm and Spd in erythrocytes, the measured value B which is the Spm amount in erythrocytes and the calculated value C of the Spd amount in erythrocytes. The values as the individual diagnostic indexes of the measured value A, the measured value B and the calculated value C are as stated above. A large number of reports will be made almost certainly in near future on specific disease conditions or physiological conditions which can effectively be diagnosed by a combination of any two items of the measured value A, the measured value B and the calculated value C or a combination of all items.

The ninth aspect of the invention is the diagnostic method according to the eighth aspect, wherein the index includes at least the calculated value C, and the diagnosis is diagnosis for prognosis of organ excision or organ transplantation.

When at least the calculated value C is included as the diagnostic index in the eighth aspect, the diagnosis for prognosis of organ excision or organ transplantation is especially preferable.

The tenth aspect of the invention is the diagnostic method according to the eighth aspect, wherein the index includes at least the measured value A, and the diagnosis is diagnosis of cancers.

When at least the measured value A is included as the diagnostic index in the eighth invention, the diagnosis of cancers is especially preferable.

The eleventh aspect of the invention is a kit for measuring polyamines in erythrocytes, comprising a polyamine oxidase having a substrate specificity to spermine and spermidine, and a highly sensitive chromogen for determining hydrogen peroxide, wherein the kit is used for measuring a total amount of spermine and spermidine in erythrocytes.

The type of above stated "highly sensitive chromogen" is not necessarily limited. However, diphenylamine-based highly sensitive chromogen is one of the most preferable chromogen.

The twelfth aspect of the invention is a kit for measuring polyamines in erythrocytes, comprising a polyamine oxidase having a substrate specificity to spermine, and a highly sensitive chromogen for determining hydrogen peroxide, wherein the kit is used for measuring an amount of spermine in erythrocytes.

The type of above stated "highly sensitive chromogen" is not necessarily limited. However, diphenylamine-based highly sensitive chromogen is one of the most preferable chromogen.

The thirteenth aspect of the invention is a kit for measuring polyamines in erythrocytes, comprising a polyamine oxidase having a substrate specificity to spermine and spermidine, a polyamine oxidase having a substrate specificity to spermine, and a highly sensitive chromogen for determining hydrogen peroxide, wherein the kit is used for calculating an amount of spermidine in erythrocytes.

The type of above stated "highly sensitive chromogen" is not necessarily limited. However, diphenylamine-based highly sensitive chromogen is one of the most preferable chromogen.

The measurement of the Spm amount and/or the Spd amount in erythrocytes can be conducted easily with good precision by using the kit for measuring polyamines in erythrocytes according to any of the eleventh to thirteenth aspects.

The above and other advantages of the invention will become more apparent in the following description and the accompanying drawing.

DETAILED DESCRIPTION OF THE INVENTION

Embodiments for performing the first to thirteenth aspects of the invention including the best embodiments thereof are described below.

[Method for Measuring Polyamines in Erythrocytes]
(Outline of the Method)

The method for measuring polyamines in erythrocytes according to the invention includes the first to third measuring methods.

The first measuring method is a method comprising reacting an eluate of erythrocytes separated and purified from blood with a polyamine oxidase having a substrate specificity to Spm and Spd, and determining hydrogen peroxide formed with a highly sensitive chromogen (for example, a diphenylamine-based chromogen) to measure a total amount of Spm and Spd in erythrocytes. In the first measuring method, conditions in reacting the eluate with the polyamine oxidase can be, in short, advantageous conditions for the activity of the polyamine oxidase. For example, when the polyamine oxidase is an oat seedling-derived polyamine oxidase (OSPO), it is preferable that pH is set at from 6 to 7, especially 6.5 and the temperature is set at from 30 to 40° C., especially 37° C.

In the first measuring method and the following second measuring method, it is preferable or necessary that a peroxidase suitable for an enzymatic reaction system is coexistent.

The second measuring method is a method comprising reacting an eluate of erythrocytes separated and purified from blood with a polyamine oxidase having a substrate specificity to Spm, and determining hydrogen peroxide formed with a highly sensitive chromogen (for example, a diphenylamine-based chromogen) to measure an Spm amount in erythrocytes.

Regarding the conditions in reacting the eluate with the polyamine oxidase in the second measuring method, it is preferable to select not only generally advantageous conditions for an enzyme but also conditions for exhibiting a substrate specificity to Spm as an enzyme most remarkably. It is especially preferable to select conditions for exhibiting a substrate specificity to Spm as an enzyme most remarkably in comparison to other in-vivo polyamines such as Spd. For example, when the polyamine oxidase is a barley seedling-derived polyamine oxidase (BSPO), it is preferable that pH is set at from 4 to 5, especially 4.5. It is preferable that the temperature is set at from 30 to 40° C., especially 37° C.

The third measuring method is a method comprising obtaining a calculated value C of an Spd amount in erythrocytes by subtracting a measured value B from a measured value A on the basis of the same sample of the same specimen. Here, the measured value A is a measured value of a total amount of Spm and Spd in erythrocytes obtained by the first measuring method, and the measured value B is a measured value of the Spm amount in erythrocytes obtained by the second measuring method.

(Preparation of Samples)

In the first measuring method and the second measuring method, a method for separating and purifying erythrocytes from blood sampled from a specimen and a method for eluting materials (protoplasms) from the erythrocytes are not limited, and any known methods including a method which was conducted in Examples to be described later can be employed. The "specimen" here referred to is not necessarily limited to humans, and may be, for example, various mammals other than humans.

(Polyamine Oxidases)

The "polyamine oxidase" referred to in the first measuring method indicates substantially an enzyme which is specifically reacted with Spm and Spd to oxidize them and form hydrogen peroxide. The type or the origin of this polyamine oxidase is not limited, and any polyamine oxidase in which the foregoing substrate specificity is observed can be used. As its preferable example, an oat (namely, oat seedling)- derived polyamine oxidase can be mentioned. There is a possibility that such a polyamine oxidase is found from gramineous plants other than oats or from any other living things.

The oat-derived polyamine oxidase used in Examples to be described later is an enzyme having FAD as a structural type and an enzyme which specifically cuts a secondary amino group in view of a reaction mechanism. As this enzyme, a reliable commercial product can be used, or it can be produced from oat seedlings by the method demonstrated in Examples to be described later.

The following "chemical formula 1" shows a reaction formula in case of reacting spermidine with the oat seedling-derived polyamine oxidase (OSPO) and a reaction formula in case of reacting spermine therewith.

(Chemical formula 1)

(Highly Sensitive Chromogen)

In the first measuring method and the second measuring method, one of the most preferable highly sensitive chromogen is the diphenylamine-based chromogen. The diphenylamine-based chromogen indicates a chemical substance which has a diphenylamine structure as a basic skeleton and is colored with a specific color by a sensitive reaction with hydrogen peroxide. The degree of coloration is measured by measurement of an absorbance in a predetermined wavelength region corresponding to the color or the like, whereby the total amount of Spm and Spd (or the Spm amount) in the sample can exactly be measured through determination of hydrogen peroxide.

As the highly sensitive chromogen, a metal salt of N-(carboxymethylaminocarbonyl)-4,4'-bis(dimethylamino)-diphenylamine is preferable. Its alkali metal salt is more preferable, and its sodium salt (DA-64) is especially preferable.

The following "chemical formula 2" shows a reaction scheme of DA-64 and hydrogen peroxide in the presence of a peroxidase (POD). In the "chemical formula 2", "Bindschedler's Green" is a green dye formed from DA-64 having a maximum absorption at 727 nm. Chemical structures of DA-64 and Bindschedler's Green are also shown under the reaction scheme.

(Chemical formula 2)

The "polyamine oxidase" referred to in the second measuring method indicates substantially an enzyme which is specifically reacted with Spm only to oxidize it and form hydrogen peroxide. The type or the origin of this polyamine oxidase is not limited, and any known polyamine oxidase in which such a substrate specificity is observed can be used. As its preferable example, a barley (barley seedling)-derived polyamine oxidase (BSPO) can be mentioned. There is a possibility that such a polyamine oxidase is found from gramineous plants other than oats or from any other living things.

The barley-derived polyamine oxidase used in Examples to be described later is, like the foregoing OSPO, an enzyme having FAD as a structural type and an enzyme which specifically cuts a secondary amino group in view of a reaction mechanism. As this enzyme, a reliable commercial product can be used, or it can be produced from barley seedlings by the method used in Examples to be described later.

A reaction formula in case of reacting spermine with BSPO is the same as that in case of reacting spermine with OSPO in the "chemical formula 1".

[Diagnostic Method]

The diagnostic method according to the invention is a method comprising conducting diagnosis of a specimen using as an index at least one of the measured value A obtained by the first measuring method, the measured value B obtained by the second measuring method and the calculated value C obtained by calculation of "A-B" on disease conditions or physiological conditions identified to be related with these indexes.

The types of the "disease conditions or physiological conditions" are not limited so long as they are identified to have a relation to the foregoing indexes with more than a certain reliability. However, the index including at least the calculated value C is applied to prognostic disease conditions or physiological conditions of organ excision or organ transplantation. Further, the index including at least the measured value A is applied to disease conditions or physiological conditions of cancer patients suffering from various malignant tumors.

In addition, the increase in polyamine concentration has been at present reported on disease conditions of infections, cirrhosis, diabetes (type I), Alzheimer disease and the like.

Accordingly, there is a possibility that the diagnostic method according to the invention is applied to these disease conditions.

[Kit for Measuring Polyamines in Erythrocytes]

The kit for measuring polyamines in erythrocytes according to the invention includes the following three types, the first to third measuring kits.

The first measuring kit comprises at least a polyamine oxidase having a substrate specificity to spermine and spermidine, and a highly sensitive chromogen (for example, a diphenylamine-based chromogen) for determining hydrogen peroxide, and the kit is used for measuring a total amount of spermine and spermidine in erythrocytes.

The second measuring kit comprises at least a polyamine oxidase having a substrate specificity to spermine, and a highly sensitive chromogen (for example, a diphenylamine-based chromogen) for determining hydrogen peroxide, and the kit is used for measuring an amount of spermine in erythrocytes.

The third measuring kit comprises at least a polyamine oxidase having a substrate specificity to spermine and spermidine, a polyamine oxidase having a substrate specificity to spermine, and a highly sensitive chromogen (for example, a diphenylamine-based chromogen) for determining hydrogen peroxide, and the kit is used for calculating spermidine in erythrocytes.

Further, the foregoing measuring kits can preferably comprise an appropriate type of a peroxidase. The polyamine oxidase or the peroxidase can be provided as, for example, a stable freeze-dried product with an appropriate solution (buffer with appropriate pH or the like) included in a separate container. Still further, these measuring kits can comprise, as will be shown in Examples later, a unit such as an appropriate ion exchange resin column. Furthermore, these measuring kits can comprise necessary or useful components which are ordinary components for these types of the measuring kits, such as a buffer solution, a neutralizing solution and a standard solution.

EMBODIMENTS

EXAMPLE 1-1

First Measuring Method 1

(Production of OSPO)

Oat seedlings which had been sprouted in a dark room for 21 days were squeezed with cold purified water, and the squeezed juice was adjusted to pH 4 with citric acid to cause precipitation. The precipitate was then centrifuged, and dissolved in a citrate buffer solution of pH 6 containing 1 mol sodium chloride. An equal amount of acetone of $-15°$ C. was added thereto to cause precipitation.

As empirically known, a coarsely purified enzyme made of this acetone precipitation fraction can be used satisfactorily as an OSPO enzyme. However, in this Example, the OSPO preparation was obtained by acetone precipitation and ammonium sulfate fractionation. Consequently, $8.32 \times 10^5$ units of a purified product of OSPO were obtained from 378 g of the oat seedlings.

Here, "1 unit" of OSPO refers to an enzyme amount in which to cause an enzymatic reaction that forms hydrogen peroxide in an amount of 1.0 nmol per minute at 35° C. This definition for "1 unit" is also applied to BSPO to be described later or other enzymes.

(Preparation of Samples)

Subjects were healthy persons, 15 males and 15 females, aged 19 to 52 years, and 46 untreated inpatients with various solid tumors, aged 23 to 62 years. As female subjects, premenopausal females were excluded due to known fluctuation in polyamine levels.

1.0 mL of a 0.5 mol/L trichloroacetic acid solution was added to 0.5 mL of packed erythrocytes obtained from hepalinized blood of each of these subjects. The mixture was stirred, and then centrifuged at 3,000 r.p.m. for 10 minutes to remove proteins. Then, 1.0 mol/L of a Tris solution [bis(2-hydroxyethyl)iminotris(hydroxyethyl)methane] was added to 0.75 mL of the supernatant obtained by the centrifugation to adjust pH to 6.5. This solution was added to a weakly acidic cation exchange resin (Bio-Rex 70, manufactured by Bio-Rad Laboratories, U.S.A.), and washed with 1.0 mL of purified water. The contents of erythrocytes were then eluted with 1.0 mL of a 0.5 mol/L trichloroacetic acid solution, and 1.0 mL of 0.285 mol/L of a Tris solution was added to the eluate to adjust pH to 6.5 and form a sample solution for measurement.

(Enzymatic Reaction)

A polyamine oxidase solution was prepared when in use by adding 40 units of a peroxidase, 0.378 mg of DA-64 (manufactured by Wako Pure Chemical) and 1,000 units of above-prepared OSPO to 10 mL of 0.1 mol/L PIPES buffer [piperazine-N,N'-bis(2-ethanesulfonic acid): pH 6.5]. The peroxidase is a horseradish-derived Type X peroxidase. 1.0 mL of this polyamine oxidase solution was added to 2.0 mL of the foregoing sample solution for measurement, and the reaction was conducted at 37° C. for 15 minutes. A green dye formed by this reaction was measured for an absorbance at 727 nm, its maximum absorption wavelength. From the results, the total amount of Spm and Spd in erythrocytes was calculated.

A blindfold test was performed in the foregoing manner using 0.5 mL of purified water in place of packed erythrocytes.

(Results of Measurement)

As a result of the foregoing measurement, the total amount of Spm and Spd in packed erythrocyte samples was distributed in the range of $25.09 \pm 4.61$ μmol/L (mean±S.D.) in 30 healthy subjects, and distributed in the range of $35.56 \pm 8.95$ μmol/L (mean±S.D.) in 46 untreated inpatients with solid tumors.

Calibration curves proved to be linear on both Spm and Spd in amounts of from 1 μmol/L to 200 μmol/L, though the detailed data were not shown. In view of the enzymatic reaction time that lapsed, the plateau was reached within approximately 5 minutes to complete the reaction. The simultaneous reproducibility showed C.V. within 5%, and the precision was good. The recovery was also as good as from 90 to 104%.

In view of the foregoing results, the results of the first measuring method clearly reflect the disease conditions of cancers, and the method is found to be effective as a diagnostic method of cancers or as at least an auxiliary diagnostic method thereof.

(Comparison with a Known Measuring Method)

Using the same packed erythrocyte samples as in the foregoing method, a total amount of Spm and Spd in the samples was measured for the foregoing 46 untreated inpatients by the HPLC method so far performed as a general measuring method, which was intricate, though.

This HPLC method is outlined as follows. That is, packed erythrocytes are first taken, and subjected to hemolysis by addition of a 1,6-diaminohexane solution (inner standard)

and one drop of Triton X-100. Subsequently, 10% trichloroacetic acid is added and mixed, and the mixture is centrifuged with a centrifugal separator to collect a supernatant. The supernatant is evaporated to dryness with a rotary evaporator, and the residue is dissolved in distilled water. The aqueous layer is then injected in HPLC for analysis. Polyamines in HPLC are detected by a fluorescent reaction with an o-phthalaldehyde reagent.

Figure 1:
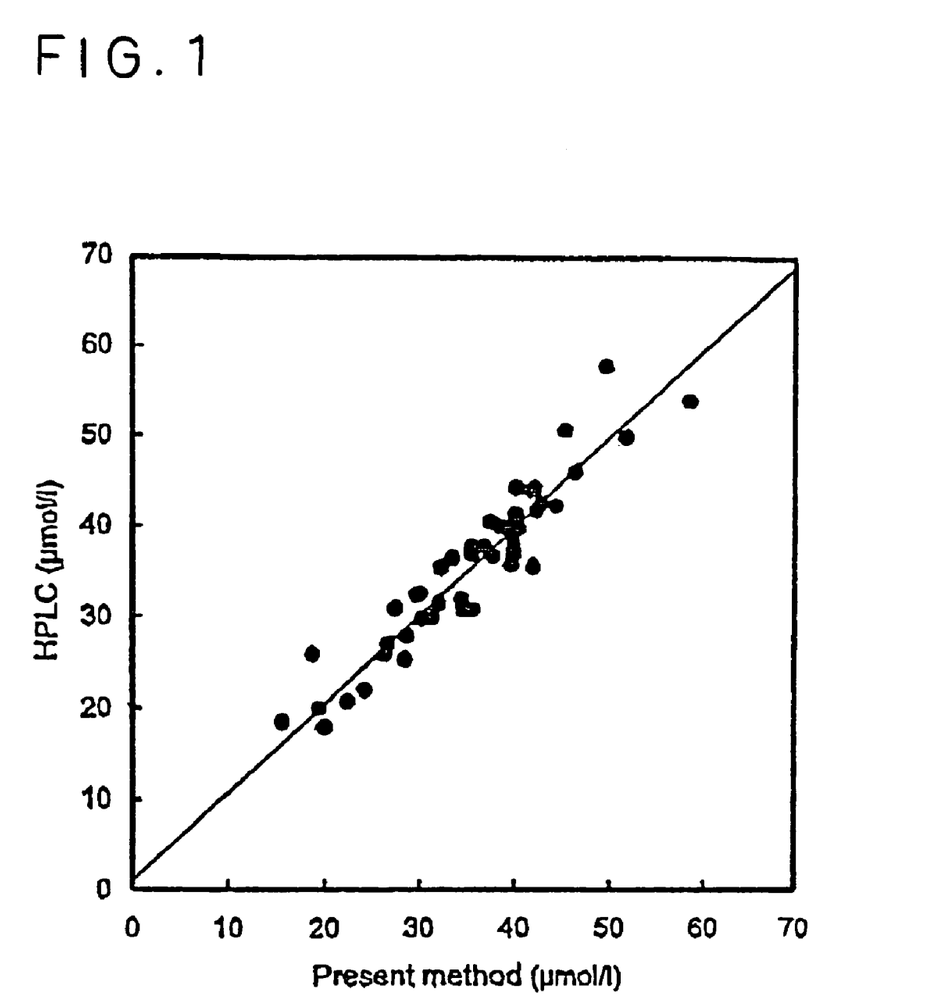
FIG. 1 is a graph showing results of measurement in EXAMPLES.

With respect to the measured value of the total amount of Spm and Spd in the samples of the 46 patients with solid tumors, the results in the measurement by the HPLC method and the results in the measurement by the first measuring method are shown in FIG. 1. In FIG. 1, plots of "black circle" indicate the measured values of the respective subjects. The positions of the plots in the ordinate direction indicate the measured values obtained by the HPLC method, and the positions thereof in the abscissa direction indicate the measured values obtained by the first measuring method respectively.

As is clear from FIG. 1, the results of measurement by the first measuring method were good with correlation coefficient r=0.944 in the correlation to the HPLC method.

(Estimation)

From the foregoing results, it has been found that the results of the first measuring method clearly reflect the disease conditions of cancers and it is effective as a diagnostic method of cancers or as at least an auxiliary diagnostic method thereof.

EXAMPLE 1-2

First Measuring Method 2

(Production of OSPO)

OSPO was produced as in the same manner described in "EXAMPLE 1-1", except for that the OSPO preparatin was obtained by acetone precipitation and purification in a usual manner using SephadexG-100, and that 1,200 units of a purified product of OSPO were obtained from 378 g of the oat seedlings.

(Preparation of Samples)

Subjects were healthy persons, 15 males and 15 females, aged 19 to 52 years, and 46 untreated inpatients with various solid tumors, aged 23 to 62 years. As female subjects, premenopausal females were excluded due to known fluctuation in polyamine levels.

0.5 mL of a 10% trichloroacetic acid solution was added to 0.5 mL of packed erythrocytes obtained from hepalinized blood of each of these subjects. The mixture was stirred, and then centrifuged at 3,000 r.p.m. for 10 minutes to remove proteins. Then, 1.0 mol/L of a Tris solution [bis(2-hydroxyethyl)iminotris(hydroxyethyl)methane] was added to 0.5 mL of the supernatant obtained by the centrifugation to adjust pH to 8. This solution was added to a weakly acidic cation exchange resin (Bio-Rex 70, manufactured by Bio-Rad Laboratories, U.S.A.), and washed with 2.0 mL of purified water. The contents of erythrocytes were then eluted with 1.0 mL of a 10% trichloroacetic acid solution, and 1.0 mol/L of a Tris solution was added to the eluate to adjust pH to 6.5 and form a sample solution for measurement.

(Enzymatic Reaction)

A polyamine oxidase solution was prepared when in use by adding 18 units of a peroxidase, 0.189 mg of DA-64 (manufactured by Wako Pure Chemical) and 50 units of above-prepared OSPO to 10 mL of 0.1 mol/L PIPES buffer [piperazine-N,N'-bis(2-ethanesulfonic acid): pH 6.5]. The peroxidase is a horseradish-derived Type X peroxidase. 2.0 mL of this polyamine oxidase solution was added to 1.0 mL of the foregoing sample solution for measurement, and the reaction was conducted at 37° C. for 15 minutes. A green dye formed by this reaction was measured for an absorbance at 727 nm, its maximum absorption wavelength. From the results, the total amount of Spm and Spd in erythrocytes was calculated.

A blindfold test was performed in the foregoing manner using 0.5 mL of purified water in place of packed erythrocytes.

(Results of Measurement)

As a result of the foregoing measurement, the total amount of Spm and Spd in packed erythrocyte samples was distributed in the range of about 25±5 μmol/L (mean±S.D.) in 30 healthy subjects, and distributed in the range of about 35±9 μmol (mean±S.D.) in 46 untreated inpatients with solid tumors.

Calibration curves showed good straight lines on both Spm and Spd in amounts of from 1 μmol/L to 200 μmol/L, though the detailed data were not shown. In view of the enzymatic reaction time that lapsed, the plateau was reached within approximately 5 minutes to complete the reaction. The simultaneous reproducibility showed C.V. within 5%, and the precision was good. The recovery was also as good as about 100%.

In view of the foregoing results, the results of the first measuring method clearly reflect the disease conditions of cancers, and the method in the EXAMPLE 1–2 is found to be effective as a diagnostic method of cancers or as at least an auxiliary diagnostic method thereof.

(Comparison with a Known Measuring Method)

The results of measurement by the first measuring method in the EXAMPLE 1–2 showed good correlation coefficient (r) in the correlation to the HPLC method, as in the EXAMPLE 1-1.

(Estimation)

From the foregoing results, it has been found that the results of the first measuring method in the EXAMPLE 1-2 clearly reflect the disease conditions of cancers and it is effective as a diagnostic method of cancers or as at least an auxiliary diagnostic method thereof.

EXAMPLE 2

Second Measuring Method

With respect to the second measuring method, comparative clinical data of healthy persons and persons in specific disease conditions or physiological conditions as in EXAMPLE 1-1 and EXAMPLE 1-2 on the first measuring method have not yet been obtained. However, regarding a barley seedling-derived polyamine oxidase BSPO, data by which various characteristics including the substrate specificity can satisfactorily be confirmed are obtained as described below. Accordingly, when the measurement is conducted at the same clinical level as in EXAMPLE 1("EXAMPLE 1" means EXAMPLE 1-1 and/or EXAMPLE 1-2 hereinafter), effective results of measurement equal to those in EXAMPLE 1 are surely obtained.

The following EXAMPLE 2 was performed by basically the same process and means as in EXAMPLE 1 except for matters which are clearly described to be different from those in EXAMPLE 1.

(Production of BSPO)

With respect to types of barley, two different types (Benkei Mugi, Shunrai) of rokujo omugi (*Hordeum vulgare* L.)

were used. Each type of barley was cultivated and sprouted in a dark room, and BSPO was produced from seedlings of each type.

The production method is an improved Smith's method. The production method is outlined as follows. First, the barley seedlings were homogenized while being cooled, and subjected to acetone precipitation, followed by adsorption using a cellulose phosphate resin. The adsorbed enzyme was eluted with a citrate buffer solution (containing sodium chloride), then precipitated with ammonium sulfate, and extracted and coarsely purified by dialysis.

(Optimum Conditions of an Enzymatic Reaction of BSPO and Substrate Specificity Thereof)

The optimum pH, enzyme concentration and reaction time of BSPOs produced from the two types of barley were obtained using Spm and Spd as a substrate.

Consequently, to sum up, with respect to the optimum pH in the enzymatic reaction of BSPO, strong activity was observed with pH of from 4 to 5 when using Spm as a substrate. Meanwhile, the increase in activity was observed with pH of from 6 to 7 when using Spd as a substrate. In addition, the activity value to Spm with pH of from 4 to 5 was a high value which was approximately 25 times the activity value to Spd with pH of from 6 to 7. Accordingly, BSPO was confirmed to have a high substrate specificity to Spm under the liquid condition of pH of from 4 to 5.

A substrate specificity of BSPO was also examined on histamine, cadaverine and putrescine. However, it was confirmed that histamine, cadaverine and putrescine do not have a substrate specificity to BSPO under conditions of pH of from 6 to 7 and pH of from 4 to 5.

(Mutual Comparison of BSPO)

Coarsely purified BSPO produced from a fixed amount of seedlings of the foregoing rokujo omugi (Shunrai) was compared with coarsely purified BSPO produced from the same amount of seedlings of Benkei Mugi with respect to the enzyme activity. Consequently, the equal activity was observed in both cases.

(Enzymatic Reaction Time of BSPO)

An enzymatic reaction was performed with BSPO having an enzyme activity of from 60 to 100 units/µL using 100 µmol/100 mL of Spm as a substrate. Then, the enzymatic reaction was completed within approximately 30 minutes.

(Calibration Curve)

When the enzyme activity of BSPO was examined using Spm as a substrate, a linear calibration curve was obtained in an amount of from 10 µmol/L to 100 µmol/L.

(Measurement of Polyamines in Erythrocytes Using BSPO)

Using hepalinized blood collected from any of the healthy subjects, the same sample solution for measurement as in EXAMPLE 1-1 was prepared. Subsequently, a polyamine oxidase solution containing BSPO derived from Benkei Mugi and a polyamine oxidase solution containing BSPO derived from Shunrai were prepared by the same method as in EXAMPLE 1.

Each of the polyamine oxidase solutions was added to the sample solution for measurement for enzymatic reaction in the same manner as in EXAMPLE 1 except that pH in the enzymatic reaction was adjusted to 4.5 with a citrate buffer solution. A green dye formed by the reaction was measured for an absorbance at 727 nm. Separately therefrom, by using the foregoing sample, the Spm amount in the sample was measured by the HPLC method.

Consequently, the results of measuring the Spm amount by the second measuring method using two types of BSPO provided approximately the same good correlation coefficient as in EXAMPLE 1 in the correlation to the results of measuring the Spm amount by the HPLC method.

(Estimation)

In view of the foregoing results considered in combination with the results in EXAMPLE 1, it has been found that the second measuring method can provide an effective diagnostic method or at least an effective auxiliary diagnostic method on specific disease conditions or physiological conditions in which the Spm amount in erythrocytes becomes an index.

It has further been found that a well-reliable value of the Spd amount in erythrocytes can be calculated by subtracting the measured value according to the second measuring method from the measured value according to the first measuring method, so long as it is based on the same sample of the same specimen.

While the preferred embodiment has been described, variations thereto will occur to those skilled in the art within the scope of the present inventive concepts which are delineated by the following claims.

What is claimed is:

1. A method for measuring polyamines in erythrocytes, comprising:
   forming hydrogen peroxide by reacting an eluate of erythrocytes separated and purified from blood with at least one polyamine oxidase having a substrate specificity to spermine and spermidine, and
   measuring the hydrogen peroxide formed by reacting the hydrogen peroxide using at least one diphenylamine-based highly sensitive chromogen to measure a total amount of spermine and spermidine in the erythrocytes,
   wherein said polyamine oxidase reacts with 1 mol of spermine to relase 1 mol of hydrogen peroxide and reacts with 1 mol of spermidine to release 1 mol of hyrdrogen peroxide, and
   wherein said polyamine oxidase is an enzyme derived from a gramineous plant.

2. The method of claim 1, wherein said polyamine oxidase is oat seedling polyamine oxidase (OSPO) or barley seedling polyamine oxidase (BSPO), or both.

3. The method for measuring polyamines in erythrocytes of claim 1, wherein the highly sensitive chromogen is a metal salt of N-(carboxymethylaminocarbonyl)-4,4'-bis (dimethylamino)-diphenylamine.

4. The method for measuring polyamines in erythrocytes of claim 3, wherein the metal salt is a sodium salt.

5. The method for measuring polyamines in erythrocytes of claim 1, wherein the eluate of erythrocytes is adjusted to pH of from 6 to 7 and from 30 to 40° C., and said polyamine oxidase is an oat seedling-derived polyamine oxidase (OSPO).

6. A method for measuring polyamines in erythrocytes, comprising:
   forming hydrogen peroxide by reacting an eluate of erythrocytes separated and purified from blood with a polyamine oxidase having substrate specificity to spermine, and
   measuring the hydrogen peroxide formed in the foregoing step by reacting the hydrogen peroxide with a diphenylamine-based highly sensitive chromogen to measure an amount of spermine in the erythrocytes, wherein the eluate of erythrocytes is adjusted to pH of from 4 to 5 and from 30 to 40° C., and said polyamine oxidase is a barley seedling-derived polyamine oxidase (BSPO).

7. The method for measuring polyamines in erythrocytes of claim 6, wherein the highly sensitive chromogen is a metal salt of N-(carboxymethylaminocarbonyl)-4,4'-bis (dimethylamino)-diphenylamine.

8. The method for measuring polyamines in erythrocytes of claim 7, wherein the metal salt is a sodium salt.

9. A method for measuring polyamines in erythrocytes, comprising: obtaining a calculated value C of a spermidine amount in erythrocytes by subtracting the following measured value B from the following measured value A on the basis of the same sample of the same specimen, wherein measured value A is the measured value of a total amount of spermine and spermidine in erythrocytes which is obtained by forming hydrogen peroxide by reacting an eluate of erythrocytes separated and purified from blood with at least one polyamine oxidase having a substrate specificity to spermine and spermidine, and measuring the amount of hydrogen peroxide formed by reacting the hydrogen peroxide with at least one diphenylamine-based highly sensitive chromogen to measure a total amount of spermine and spermidine in the erythrocytes, wherein said polyamine oxidase reacts with 1 mol of spermine to release 1 mol of hydrogen peroxide and reacts with 1 mol of spermidine to release 1 mol of hydrogen peroxide, and wherein said polyamine oxidase is an enzyme derived from a gramineous plant; and wherein measured value B is the measured value of spermine in erythrocytes which is obtained by reacting an eluate of erythrocytes separated and purified from blood with a polyamine oxidase having substrate specificity to spermine, and determining the amount of hydrogen peroxide formed by reacting the hydrogen peroxide with a diphenylamine-based highly sensitive chromogen to measure an amount of spermine in the erythrocytes, wherein the eluate of erythrocytes is adjusted to pH of from 4 to 5 and from 30 to 40° C., and said polyamine oxidase is a barley seedling-derived polyamine oxidase (BSPO).

10. A diagnostic method comprising:

conducting diagnosis of a specimen using as an index at least one of the measured value A, the measured value B and the calculated value C as defined in claim 9 on disease conditions or physiological conditions identified to be related with these indexes.

11. The diagnostic method as claimed in claim 10, wherein the index includes at least the calculated value C, and the diagnosis is for prognosis of organ excision or organ transplantation.

12. The diagnostic method as claimed in claim 10, wherein the index includes at least the measured value A, and the diagnosis is diagnosis of cancer.

* * * * *